United States Patent [19]

Winter, III

[11] 4,072,730
[45] Feb. 7, 1978

[54] PROCESS FOR ALKYLATING AROMATIC HYDROCARBONS

[75] Inventor: George R. Winter, III, Mount Prospect, Ill.

[73] Assignee: UOP Inc., Des Plaines, Ill.

[21] Appl. No.: 754,927

[22] Filed: Dec. 28, 1976

[51] Int. Cl.$^2$ ................................................ C07C 3/54
[52] U.S. Cl. ............................. 260/671 R; 260/671 B; 260/683.48
[58] Field of Search ............ 260/671 R, 671 B, 683.48

[56] References Cited

U.S. PATENT DOCUMENTS

| 2,556,644 | 6/1951 | Brooke et al. | 260/671 B |
| 2,851,503 | 9/1958 | Shiffler | 260/671 B |
| 2,995,612 | 8/1961 | Hervert | 260/683.48 |
| 3,950,448 | 4/1976 | Witt | 260/671 B |

Primary Examiner—Delbert E. Gantz
Assistant Examiner—C. E. Spresser
Attorney, Agent, or Firm—James R. Hoatson, Jr.; John F. Spears, Jr.; William H. Page, II

[57] ABSTRACT

Aromatic hydrocarbons are reacted with olefins using hydrogen fluoride as a catalyst in a process having two reaction zones and settling zones in sequence. The initial admixture of the aromatic hydrocarbons, olefins and catalyst is effected by passing all three materials directly into a centrifugal pump utilized to recirculate liquid hydrogen fluoride from a settling zone. The pump forms the first reaction zone.

5 Claims, 1 Drawing Figure

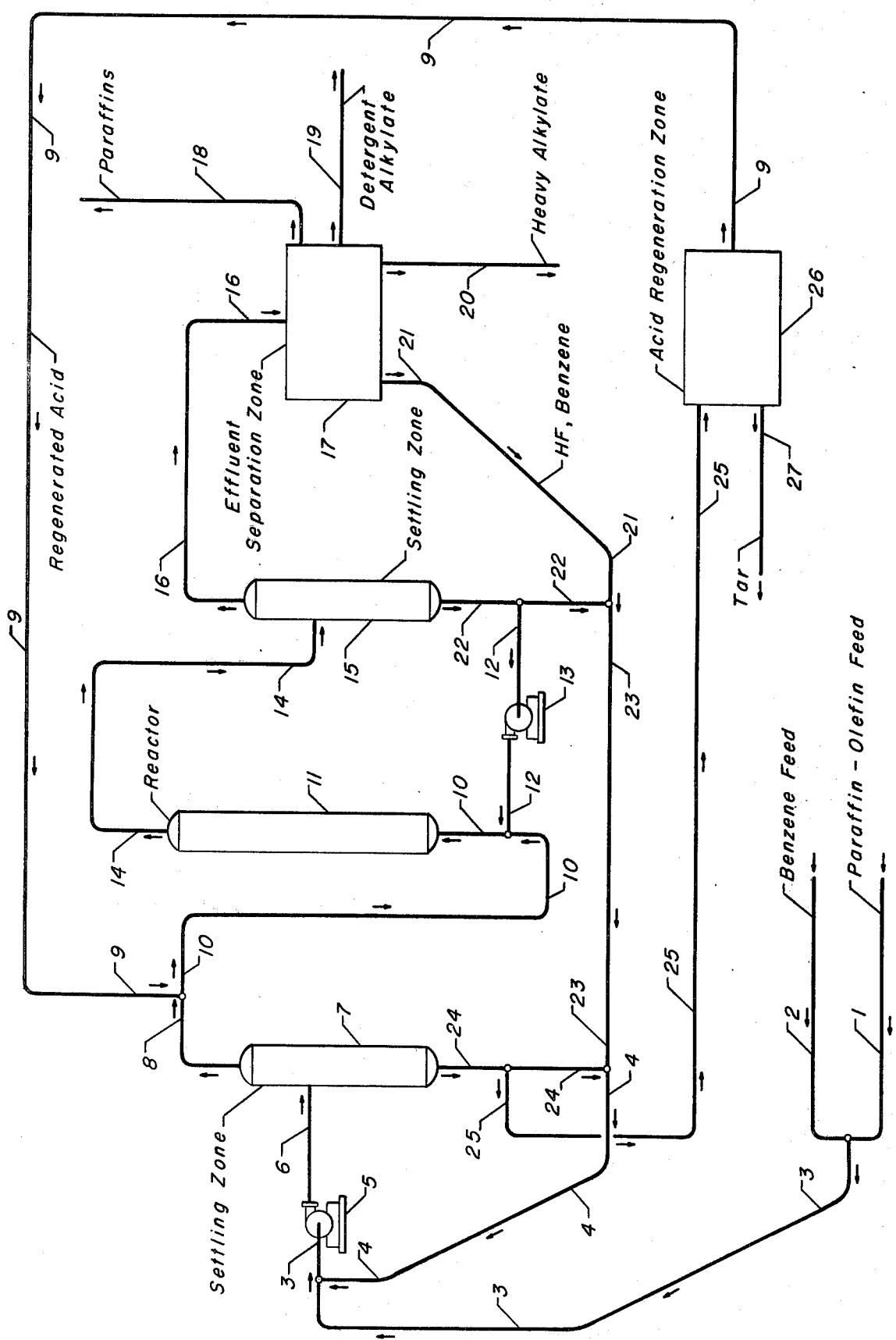

PROCESS FOR ALKYLATING AROMATIC HYDROCARBONS

FIELD OF THE INVENTION

The invention relates to the field of mineral oil conversion processes and to the chemical conversion of hydrocarbons. The invention more specifically relates to the alkylation of aromatic and other carbon compounds by the introduction of an acyclic side chain using a catalyst comprising hydrogen fluoride. It is directly concerned with a process for the production of linear alkylbenzenes for use in detergent manufacture by the reaction of mono-olefins and benzene.

PRIOR ART

The use of hydrogen fluoride as a catalyst is well established in the art. It has been used to promote the alkylation of both aromatic hydrocarbons and saturated hydrocarbons with olefins. A representative example of the state of the art is supplied by U.S. Pat. No. 3,950,448 (Cl. 260-671B). This reference describes the production of soft detergent alkylate using a two reaction step, two settling zone system similar to that utilized herein. It also describes the regeneration of the HF acid used as catalyst and the purification of the products produced in the process. U.S. Pat. No. 3,494,971 (Cl. 260-671) is another example of a two reaction step process for producing detergent alkylates. The processes presented in these two references both utilize two separate reaction vessels, with the effluent of each reaction vessel being discharged into a settling vessel. In both of these processes the feed streams and recycled benzene are not taught as being passed into the pump used to recirculate the HF acid phase removed from the bottom of the first settling zone.

The HF catalyzed alkylation of naphthalene is described in U.S. Pat. No. 3,637,884 (Cl. 260-671). The HF catalyzed alkylation of paraffins with low molecular weight olefins to produce high octane motor fuel components is described in U.S. Pat. No. 3,830,865 (Cl. 260-671) and is well established in the art.

BRIEF SUMMARY OF THE INVENTION

The invention provides a process for the HF acid catalyzed alkylation of hydrocarbons wherein the reactants and the HF acid are fed to the suction of a centrifugal pump to effect an initial mixing and reaction. In the preferred embodiment the centrifugal pump is used to recirculate a liquid acid phase stream removed from the settling zone into which the effluent of the pump is discharged. The reaction vessel which was previously used to admix the reactants and the HF acid may therefore be eliminated, and the capital costs of building a process unit may be reduced. Other advantages and embodiments will be apparent to those skilled in the art and include those set out below.

DESCRIPTION OF THE DRAWING

The Drawing illustrates the preferred embodiment of the invention. For clarity and simplicity, various subsystems and apparatus normally required for the successful operation of the process have not been shown. These items include flow and pressure control valves, control and monitoring systems, reactor internals, etc., which may be of customary design. This representation of the preferred embodiment is not intended to preclude from the scope of the invention those other embodiments set out herein or which are the result of reasonable and normal modification of these embodiments.

Referring now to the Drawing, a liquid phase feed stream of relatively pure benzene in line 2 is admixed with a combined feed stream of paraffins and monoolefins in line 1. This forms a liquid hydrocarbon stream passed through line 3. This liquid stream is combined with a liquid-phase recycle stream comprising HF and benzene stream from line 4 and then promptly passed into a centrifugal pump 5. The action of the pump is effective to achieve a high degree of mixing of the various entering chemicals. As the alkylation reaction is rapid, it is at least partially performed within the pump. The effluent of the pump therefore contains some alkylated benzene. The highly mixed pump effluent is passed through line 6 into a first phase settling zone 7. The alkylation reaction will also be occurring in line 6, and the maintenance of a high degree of admixture within this line may be ensured through the use of optional inline mixing devices.

Settling zone 7 functions as a liquid-liquid phase separator wherein the less dense hydrocarbonaceous materials form an upper liquid phase. This upper liquid phase contains unreacted benzene, paraffins and the alkylate produced in the pump and transfer line 6. A stream of this material is removed in line 8 and admixed with regenerated acid from line 9. The resulting admixture is carried by line 10 to the junction with line 12, at which it is admixed with a stream of recirculated acid. The thus formed stream is then passed upward through a reaction vessel 11 wherein it is maintained in an agitated state. The effluent of the reaction vessel is passed through line 14 to a second settling zone 15. A second phase separation operation produces an alkylate containing hydrocarbon stream which is removed in line 16 and a liquid phase acid stream removed in line 22. This acid stream is divided into two portions, one of which is recirculated through line 12 by use of recycle pump 13. The second portion of this stream continues through line 22 for eventual passage to pump 5.

The alkylate containing stream of line 16 is passed into an effluent separation zone 17, which may be one of the several types known in the art. This zone effects the separation of the entering alkylate containing stream into a product stream of a detergent-grade alkylate removed in line 19 and a stream of paraffins which is rejected in line 18. The paraffins may be passed into a dehydrogenation zone to form the olefin-paraffin feed stream entering the process in line 1. Heavy alkylates unsuitable for use as detergents are rejected in line 20. A recycle stream comprising unreacted benzene and HF is removed from the separation zone in line 21 and admixed with the acid from the second settling zone carried by line 22. To this combined acid-benzene stream, which is transferred by line 23, is added the acid from the first settling zone from line 24. The total resulting recycle stream is carried by line 4 and admixed with the feed material from line 3. A second portion of the acid from the first settling is passed through line 25 into an acid regeneration zone 26. It is therein purified by the removal of high boiling hydrocarbonaceous compounds referred to as tar or acid-soluble oils. This tar is removed from the process in line 27, and the regenerated acid is returned to the process in line 9. A benzene drag stream may also be removed from the process by a line not shown to limit the buildup of impurities in the recycled benzene.

DETAILED DESCRIPTION

The alkylation of hydrocarbons is a process used in the chemical and petroleum industries to produce various products and intermediates. Hydrofluoric acid (HF) is used as the catalyst in several of these processes. One of the more important HF acid catalyzed alkylation reactions is the production of detergent grade alkylated aromatic hydrocarbons. This "detergent alkylate" is formed by the reaction of an aromatic hydrocarbon with an olefinic hydrocarbon having from about 6 to 20 carbon atoms per molecule. A better quality detergent precursor normally results from the use of olefinic hydrocarbons having from 10 to 15 carbon atoms per molecule. The preferred aromatic hydrocarbon is benzene, but other hydrocarbons including toluene, the xylenes and ethylbenzene may also be reacted according to the subject process.

The detergents produced from the resulting alkylated hydrocarbons are classified either as "soft" if they are biodegradable with relative ease or as "hard" if they are relatively non-biodegradable. Soft detergents are the result of using a long-chain normal mono-olefin as the olefinic reactant. The preferred method of producing these olefins is by the dehydrogenation of the corresponding paraffins. Dehydrogenation processes typically do not provide a 100% conversion of the paraffins to olefins, and the separation of olefins and paraffins of the same carbon number requires considerable capital expenditure. It is therefore a common practice to utilize an unseparated paraffin/olefin effluent stream of the dehydrogenation zone as a feed stream to the alkylation zone. The non-reactive paraffins pass through the alkylation zone in the various hydrocarbon-phase streams.

This integration of dehydrogenation zones and alkylation zones is described in U.S. Pat. Nos. 3,413,373; 3,484,498; and 3,494,971 (all Cl. 260-671). Hard detergents result from the use of propylene tetramer produced in a catalytic condensation process as the olefinic hydrocarbon. As the use of soft detergents is becoming more widespread, the subject invention will be discussed primarily in terms of soft detergent production.

Reactions which involve olefinic hydrocarbons and are catalyzed by HF usually proceed at a very fast rate. To reduce the amount of olefin polymerization and to promote the production of mono-alkylated products, the reactants are normally subjected to vigorous agitation and mixing at the initial contacting of the olefinic reactant with the HF and aromatic hydrocarbon. This is an attempt to cause a uniform dispersion and intimate contacting of the hydrocarbon and acid phases and to avoid the formation of "hot spots" having high temperatures or high HF concentrations. The initial contacting is done in a number of different ways in the prior art. For instance, the olefinic hydrocarbons may be sprayed into a mast of acid-hydrocarbon through nozzles or pulled through eductors. After this initial mixing it is customary to pass the just mixed reactants and HF upwardly through a reaction vessel containing apparatus to further agitate or admix the liquids. It is an objective of this invention to provide a process for the HF catalyzed alkylation of hydrocarbons wherein the reactants are admixed to a high degree soon after their initial contact. It is a further objective to provide a process for the production of detergent-grade alkylated aromatic hydrocarbons. It is another objective of the invention to provide a two stage detergent-alkylate process which does not require a separate reaction vessel for the initial olefin-aromatic hydrocarbon reaction.

In the preferred type of aromatic hydrocarbon alkylation process the hydrocarbon stream passing through the two reaction zones is contacted with two liquid-phase HF acid streams in sequence. The first contacting step or stage is performed in a manner chosen to effect the initial alkylation of the aromatiic hydrocarbon, and the second contacting step is conducted to cause product improvement as by the decomposition of any alkyl-fluorides produced in the first contacting step. Different acid streams are used for these two steps. These two acid streams are formed in part by the recirculation of acid phase material produced in their respective settling zones. It is therefore necessary to provide recirculation pumps which pressurize the recirculated acid sufficiently to cause it to flow through the contacting and settling zones and their associated piping. According to prior art methods the recirculated acid streams were pressurized in these pumps prior to their admixture with the hydrocarbon streams.

It has now been discovered that the centrifugal pump used to recirculate the acid fed to the first contacting step may be utilized as an effective mixing device suitable for the initial contacting of the olefinic hydrocarbon with the HF acid and the hydrocarbon to be alkylated. The degree of mixing in the pump may be sufficient to completely eliminate the need for a separate reaction vessel upstream of the first settling zone. The invention may be viewed as a method which allows the utilization of the kinetic energy required for mixing at its source rather than in a downstream reaction vessel. That is, the energy previously required to create the turbulence necessary for mixing in the reaction vessel is instead utilized at its source.

In order to avoid the undersirable lengthy contact of the olefinic hydrocarbon and the acid in an unmixed state, the olefinic hydrocarbon should be added to the acid recirculation stream at a point just upstream of the pump. This close coupling of the olefin feed line to the suction of the pump should not result in any greater amount of undesirded reactions than the prior art methods wherein these two streams are initially joined at points just outside of a reaction vessel. The pumps are to be centrifugal pumps as they deliver excellent mixing. Positive displacement pumps do not provide the same degree of mixing and are therefore much less desirable. The pump chosen for usage in the process may be adapted for use as a reaction mixing zone by mechanical modification. This may include a special arrangement of the inlet or inlets to allow close coupling to the two lines carrying the materials to be admixed. Another suitable modification is the addition of a water jacket to remove the heat of mixing and heat of reaction in exothermic reactions. The size, materials of construction, impeller design, etc. may be chosen in the customary manner by those skilled in the art.

As the initial reaction of the olefinic hydrocarbon with the aromatic hydrocarbon will be occurring in the pump, the material entering and within the pump will be maintained at alkylation promoting conditions. The amount of alkylation which occurs in the pump and the transfer line carrying the effluent of the pump to the first settling zone should consume at least 98 wt. % of the entering olefinic hydrocarbon. Inline mixing devices, such as static mixers and mixing valves, may be utilized in the transfer line to keep the reactants admixed until they are passed into the settling zone. As an alternative to this preferred mode of operation, the effluent of the pump may be passed into a reaction vessel. This mode of operation can be utilized when it is desired to maintain the acid and hydrocarbon phases in contact for a significant length of time during or just after the first reaction step. For instance, U.S. Pat. No. 3,830,865 (Cl. 260-671R) describes the use of a "reaction soaker" between the reactor and settler used in a motor fuel alkylation process.

When used in reference to the alkylation of aromatic hydrocarbons, the term "alkylation promoting conditions" is intended to include a pressure sufficient to maintain the reactants and HF in a liquid phase. A general range of operating pressures is from about 2 to 41 atmospheres abslute. The pressure must be sufficient to maintain liquid phase conditions and to prevent cavitation within the pump. A pressure above 25 psig. is preferred. The temperature range covered by this set of conditions is from about $-20°$ to about 95° C., but the reaction is preferably conducted at a temperature of from 15° to 50° C. The volumetric ratio of liquid phase HF to the total amount of hydrocarbons entering the pump should be maintained with the broad range of from about 0.2:1.0 to about 10.0:1.0. A preferred range for this ratio is from 1.0:1.0 to 2.5:1.0. To lessen the production of polyalkylated aromatics and also to reduce the amount of olefin polymerization in the first reaction step, the mole ratio of the aromatic hydrocarbon to the olefinic hydrocarbon at point of initial olefin-acid contact is maintained above 1.0:1.0 but preferably below 10.0:1.0. A typical commercial ratio for this contacting step is from 3.0:1.0 to 8.0:1.0

This set of alkylation promoting conditions is adjusted to a limited extent for the second acid contacting or reaction step. The same pressure range may be used, but a higher temperature is preferred. This higher temperature should be at least 6 centigrade degrees above that used in the first acid-hydrocarbon contacting step. All temperatures given herein are intended to refer to the avarage temperature of the liquid stream entering the respective downstream settling zone. The acid-to-hydrocarbon volume ratio in the second contacting step will normally be slightly lower, and a typical ratio is about 1.0:1.0. Preferably, the purity of acid used in the second contacting step will be higher than that used in the first step. This is preferred because of the better effectiveness of higher purity acid for the treatment of the alkylate. A higher acid purity is obtained by admixing the newly regenerated acid with the alkylate containing stream entering the second stage reaction zone. Makeup acid for use in the first contacting step is withdrawn from the second settling zone and therefore contains a higher concentration of the high molecular weight hydrocarbonaceous compounds referred to as tar. The acid used in the first contacting step may be from about 85 to 92 wt.% HF and will typically be about 90wt.%. The acid used in the second contacting step preferably contains more than 90 wt.% HF and is typically about 93 to 94 wt.% HF.

The two settling zones will normally be maintained at a temperature set by the entering HF-hydrocarbon mixtures. They will therefore be at substantially the same temperature as the immediately upstream contacting step. The same is also normally true for the pressures used in the settling zones after adjustment for pressure change due to liquid flow and elevation differences. The settling zones may however be downstream of control valves and therefore operated at a somewhat reduced pressure. This reduced pressure however must be superatmospheric and sufficient to maintain liquid phase conditions. A pressure above 20 psig. but below 500 psig. is preferred. The residence time of either acid or hydrocarbon phases in the settling zone should be in excess of 10 minutes but less than 30 minutes.

The operating conditions required for regeneration of the HF acid-catalyst are well known to those skilled in the art. It is described in the literature such as the previously cited patents and also in U.S. Pat. No. 3,721,720. This operation is normally accomplished by stripping the acid under conditions sufficient to decompose alkyl-fluorides and produce an overhead vapor stream containing HF and the stripping media. Benzene available within the process is a suitable stripping media. The overhead vapors of the stripping column are condensed to form an acid phase and benzene phase containing dissolved HF. The acid phase is withdrawn as the regenerated HF stream carried in line 9. The benzene phase is normally charged to the first reaction or contacting step in admixture with the other hydrocarbon steams.

The previously cited patents also describe fractionation systems and conditions suitable for use as effective effluent separation zones used to recover the product alkylate from the hydrocarbon phase removed from the second settling zone. In one system for the separation of the effluent of the second settler, this effluent stream is passed into an upper portion of a first fractionation column which is operated under conditions effective for the stripping of hydrogen fluoride from the entering hydrocarbonaceous liquid. The resultant overhead stream of this column comprises hydrogen fluoride and some benzene which may be passed into the overhead system of the fractionation column used for the regeneration of the HF. The bottoms stream of this HF stripper is passed into a second fractionation column referred to as a benzene column. This column is operated under conditions effective to cause the division of the entering hydrocarbons into a high purity benzene stream which is removed as the overhead liquid and a bottoms stream containing the alkylate product. This bottoms stream is passed into a third fractionation column referred to as a paraffin column. The non-reactive paraffins are removed as an overhead liquid stream. The bottoms stream of the third fractionation column comprises the product alkylate and any higher molecular weight hydrocarbons formed by side reactions. This bottoms stream is passed into a fourth fractionation column which produces a high purity overhead stream containing the detergent alkylate. A bottoms stream comprising polymerized olefins and polyalkylated benzenes is removed for disposal. The third and the fourth fractionation columns are normally operated at a subatmospheric pressure. An alternative method of performing this separation is disclosed in U.S. Pat. No. 3,950,448.

In accordance with this description the preferred embodiment of the invention may be characterized as a process for the production of linear alkylaromatic hydrocarbons which comprises the steps of passing a feed stream comprising an aliphatic mono-olefin having from 10 to 15 carbon atoms per molecule and a recycle stream comprising liquid-phase hydrogen fluoride and benzen into and through a centrifugal pump maintained at alkylation promoting conditions and thereby forming a pump effluent stream, passing the pump effluent stream into a first settling zone and effecting the phase separation of the pump effluent stream into a first acid stream comprising liquid phase hydrogen fluoride and a first hydrocarbon stream comprising benzene and an alkylbenzene, passing a portion of the first acid stream into the pump as the recycle stream, admixing the hydrocarbon stream with a second acid stream comprising liquid phase hydrogen fluoride within a reaction zone maintained at alkylation promoting conditions to form a reaction zone effluent stream comprising benzene, the alkylbenzene, and hydrogen fluoride, passing the reaction zone effluent stream into a second settling zone and effecting the phase separation of the reaction zone effluent stream into a third acid stream comprising liquid phase hydrogen fluoride and a second hydrocarbon stream comprising dissolved hydrogen fluoride, benzene, and the alkylbenzene, and separating benzene and hydrogen fluoride from the second hydrocarbon stream to form a product stream comprising the alkylbenzene.

The subject invention is one of general application to the art of HF catalyzed reactions. As such it may be applied to the alkylation of hydrocarbons other than aromatics, as well as to processes in which there is only one contacting or reaction step as compared to the two of the preferred detergent alkylate process. One such application of the subject invention is the production of gasoline blending components by the reaction of an isoparaffin and an olefin. This process requires intimate and quick admixture of the reactants with recirculated and/or fresh HF acid. Typical feed components to this process include isobutane and isopentane as the isoparaffins and propylene, butylene, amylenes or olefin-acting compounds such as $C_3$-$C_5$ alkyl halides as the olefin. Conditions and apparatus for this process are known to those skilled in the art, and further details of the process may be obtained from such references as U.S. Pat. Nos. 3,830,865; 3,607,970; 3,501,536; 3,825,617 and 3,729,526.

In the preferred detergent alkylation process the total feed stream to the reaction zone contains a large amount of benzene and normal paraffins which will not take part in the reaction. These materials act as a heat sink which limits the temperature increase caused by the exothermic alkylation reaction. The recirculated acid phase material may also be used as a heat sink. In a motor fuel alkylation process there will be no benezene present, and the amount of isoparaffin present may not greatly exceed the amount of the olefin. Therefore, in the embodiment of this invention directed to motor fuel production, a material used as a heat sink is formed by recycling a cooled portion of the effluent of the pump to the suction of the pump. The total effluent of the pump may be cooled or just the portion which is split off for recycling may be cooled. The net effluent of the pump is passed into a reaction soak zone.

The invention is not limited to practice in systems in which hydrogen fluoride is utilized as the sole catalytic agent. For example, the hydrogen fluoride may be admixed with other halogen-containing catalytic agents, such as boron trifluoride. U.S. Pat. No. 3,761,540 (Cl. 260-683.51) describes a process using such a mixture to effect the alkylation of an isoparaffin with an olefin. The catalyst used therein contains from about 0.3 to about 4.0 wt.% $BF_3$. Such catalyst systems may also be used to effect reactions of aromatic hydrocarbons including benzene, toluene and the xylenes. These reactions may include alkylation with both straight chain and branched chain olefins or inorganic chemical compounds including carbon oxides. For instance, the subject invention may be utilized for the production of tolyaldehyde by the reaction of toluene and carbon monoxide with hydrogen fluoride and boron trifluoride being used as the catalyst. This reaction may be performed by several different methods, such as those described in U.S. Pat. Nos. 2,534,017; 3,948,998 and 3,962,343. In general, a temperature of from about $-30°$ to $40°$ C. and a superatmospheric pressure of from about 5 to 60 atmospheres may be used. 2,4-dimethyl benzaldehyde and 2,4,5-trimethyl benzaldehyde may also be formed by using this catalyst system to react carbon monoxide with m-xylene and pseudocumene respectively.

In general, the subject process is useful for the performance of any fluid phase, that is either liquid or vapor phase, reaction in which it is desirable to rapidly admix the reactants or to admix the reactants with a fluid catalyst. It is especially useful where the reaction or the admixture is exothermic and it is desired to eliminate high temperature regions caused by poor mixing. Among the processes which may be performed according to the disclosed method are the nitration of olefins and aromatics, the halogenation or oxygenation of these or other hydrocarbons and similar classes of reactions. Different conditions and catalysts may be required for these other processes. This information is available in the literature and customary pressures, temperatures and reactant concentrations may be utilized.

U.S. Pat. No. 3,637,884 (Cl. 260-671) describes the hydrogen fluoride catalyzed alkylation of naphthalene with an olefin-acting compound such as organic halides, olefins and alcohols. Preferably, the olefinacting compound is a $C_3$-$C_4$ mono-olefin. Also applicable, however, are ethylene and cyclo-olefins including cyclohexene and cyclopentene. This reference describes the effects of temperature on specific isomer production and indicates the reaction may be conducted between $0°$ and about $100°$ C. The conditions employed are generally similar to that described above for detergent alkylation. For instance, the mole ratio of the olefin to naphthalene is maintained above 1.0:1.0 to reduce polymerization and the reaction temperature and pressure are correleated to maintain liquid phase conditions.

I claim as my invention:

1. In the alkylation of an aromatic hydrocarbon with an olefinic hydrocarbon in contact with hydrogen fluoride catalyst, wherein the resultant reaction mixture is separated in a settling zone into a hydrocarbon phase and a liquid hydrogen fluoride phase, at least a portion of which is recirculated by a centrifugal pump to the alkylation reaction, the improvement which comprises introducing the aromatic and olefinic hydrocarbons to be reacted into the centrifugal pump and therein admixing the same with hydrogen fluoride to partially alkylate said aromatic hydrocarbon with said olefin hydrocarbon, discharging the pump effluent through a restricted transfer line into said settling zone, and continuing the aromatic alkylation during the passage of the pump effluent through said transfer line to the settling zone.

2. The improvement of claim 1 further characterized in that said hydrocarbon phase from the settling zone is admixed with additional hydrogen fluoride catalyst, the mixture maintained at alkylation promoting conditions and thereafter separated into a hydrocarbon phase and a hydrogen fluoride phase, and at least a portion of the latter supplied to said centrifugal pump.

3. The improvement of claim 1 further characterized in that said aromatic hydrocarbon is benzene.

4. The improvement of claim 1 further characterized in that said olefinic hydrocarbon is a mono-olefin of from 6 to 20 carbon atoms.

5. The improvement of claim 2 further characterized in that said aromatic hydrocarbon is benzene and said olefinic hydrocarbon is a mono-olefin of from 6 to 20 carbon atoms.

* * * * *